(12) United States Patent
Lan

(10) Patent No.: US 10,899,697 B2
(45) Date of Patent: *Jan. 26, 2021

(54) MATERIAL FOR VERTICAL ALIGNING AGENT

(71) Applicant: Shenzhen China Star Optoelectronics Technology Co., Ltd., Guangdong (CN)

(72) Inventor: Song Lan, Guangdong (CN)

(73) Assignee: SHENZHEN CHINA STAR OPTOELECTRONICS TECHNOLOGY CO., LTD., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/329,375

(22) PCT Filed: Jan. 16, 2017

(86) PCT No.: PCT/CN2017/071284
§ 371 (c)(1),
(2) Date: Feb. 16, 2018

(87) PCT Pub. No.: WO2018/120325
PCT Pub. Date: Jul. 5, 2018

(65) Prior Publication Data
US 2019/0308926 A1      Oct. 10, 2019

(30) Foreign Application Priority Data
Dec. 29, 2016 (CN) .......................... 2016 1 1247733

(51) Int. Cl.
*C07C 69/618* (2006.01)
*C07C 69/732* (2006.01)
(Continued)

(52) U.S. Cl.
CPC .......... *C07C 69/618* (2013.01); *C07C 69/593* (2013.01); *C07C 69/732* (2013.01);
(Continued)

(58) Field of Classification Search
CPC ... C07C 69/618; C07C 69/593; C07C 69/732; C07C 69/65; C09K 19/56;
(Continued)

(56) References Cited

U.S. PATENT DOCUMENTS 10,100,256 B2 * 10/2018 Lan ........................ C09K 11/025
10,151,951 B2 * 12/2018 Lan ..................... G02F 1/133703
(Continued)

FOREIGN PATENT DOCUMENTS

CN      103119128 A      5/2013
CN      103492531 A      1/2014
(Continued)

OTHER PUBLICATIONS

International Search Report and Written Opinion for International Application No. PCT/CN2017/071284, dated Jan. 16, 2017.
(Continued)

*Primary Examiner* — Eli D. Strah

(57) ABSTRACT

Disclosed is a material for a vertical aligning agent, and a molecular structure of the material is shown in formula (I):

$$R-L1\underset{n}{\underbrace{[-P-L2-]}}Q \qquad (I)$$

wherein Q is a polar anchor group, L1 is a rigid group, P is a polymerizable group, L2 is a linking group, R is a terminal flexible group, and n is in a range from 1 to 3. In the material, the polar anchor group is connected to the polymerizable group, which is beneficial to increase an aspect ratio of the material. Therefore, a fluid viscosity of the material can be reduced, and a diffusion effect of the material on a substrate can be improved.

1 Claim, 1 Drawing Sheet

(51) Int. Cl.
*G02F 1/1337* (2006.01)
*C09K 19/56* (2006.01)
*C07C 69/593* (2006.01)

(52) U.S. Cl.
CPC ........ *C09K 19/56* (2013.01); *G02F 1/133711* (2013.01); *B32B 2457/202* (2013.01); *C09K 2323/02* (2020.08)

(58) Field of Classification Search
CPC .......... C09K 2323/02; G02F 1/133711; G02F 2001/133742; B32B 2457/202; Y10T 428/1005
See application file for complete search history.

(56) References Cited

U.S. PATENT DOCUMENTS 10,545,380 B2 * 1/2020 Lee .................. C09K 19/56
2008/0069968 A1 * 3/2008 Cherkaoui ............ C07C 229/60
427/487
2014/0049739 A1 2/2014 Hwang et al.
2018/0079960 A1 3/2018 Lan
2018/0120650 A1 5/2018 Lan

FOREIGN PATENT DOCUMENTS

| CN | 104830348 A | | 8/2015 | |
|---|---|---|---|---|
| CN | 105733557 A | * | 7/2016 | ........... C09K 11/025 |
| CN | 105733557 A | | 7/2016 | |
| CN | 105885872 A | | 8/2016 | |
| CN | 105974683 A | | 9/2016 | |

OTHER PUBLICATIONS

Chinese Office Action and Search Report for Chinese Patent Application No. 201611247733.0, dated Sep. 18, 2018.

* cited by examiner

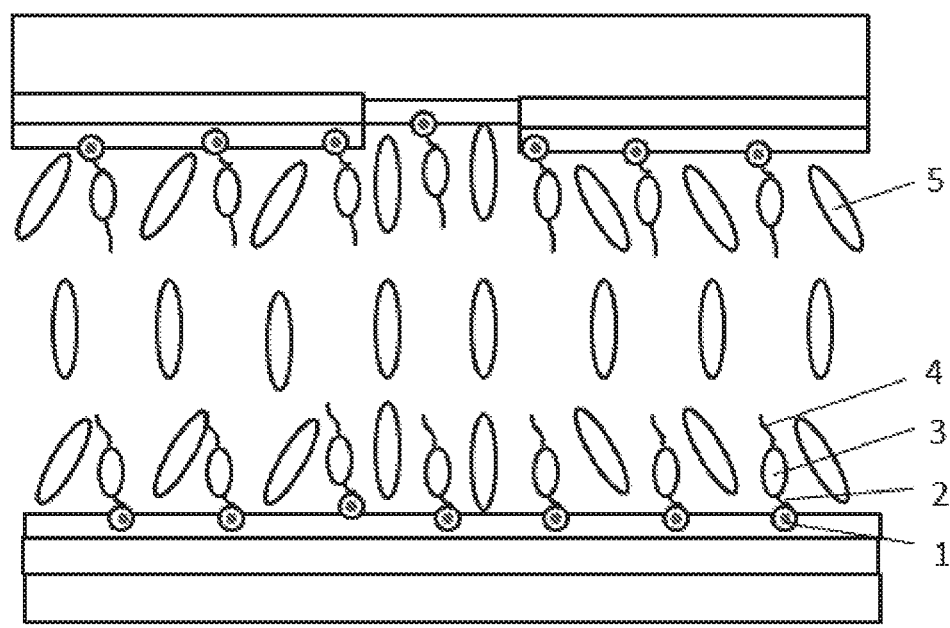

MATERIAL FOR VERTICAL ALIGNING AGENT

CROSS-REFERENCE TO RELATED APPLICATIONS

This application claims the priority of Chinese patent application CN 201611247733.0, entitled "Material for vertical aligning agent" and filed on Dec. 29, 2016, the entirety of which is incorporated herein by reference.

FIELD OF THE INVENTION

The present disclosure relates to the field of liquid crystal aligning material, and in particular, to a material for a vertical aligning agent.

BACKGROUND OF THE INVENTION

A color filter (CF) substrate and a thin film transistor (TFT) substrate of a liquid crystal display (LCD) device are respectively covered with a thin film material layer, and a main role thereof is to align liquid crystal molecules in a certain direction. It is called as an alignment film and polyimide (PI) is commonly selected as a material thereof. The alignment film is mainly divided into a rubbing alignment PI material and a photoalignment PI material. However, both of the two alignment materials have disadvantages. First, the rubbing alignment material may have problems such as dust particles, electrostatic residual, and brush marks, which lead to decrease of a qualified rate of a product. The problems can be avoided in the photoalignment material. However, the optical alignment PI material has a poor heat resistance and aging resistance, and a weak ability to anchor LC molecules, and thus a quality of the panel will be affected. Second, the PI material itself has high polarity and water-absorbing capacity, and properties thereof would be easily changed during storage and transportation procedures, which will lead to uneven alignment of the liquid crystal. Besides, the PI material is expensive, and a film forming procedure is quite complicated on a thin film transistor liquid crystal display (TFT-LCD) device. As a result, cost of a panel will be increased. Third, a large amount of N-methyl-pyrrolidone (NMP) solvent is contained in a PI solution. As a result, a manufacturing procedure of the alignment film requires high energy consumption, which is harmful to environment and human health. In addition, due to problems such as unevenness of the alignment film, lack of coating, low viscosity, and foreign bodies, the qualified rate of the product will be affected, which leads to a waste of resources and increase of manufacturing cost.

Therefore, in the TFT-LCD device, cost of manufacturing the panel can be greatly reduced if the LC molecules can be aligned without a PI film. However, in the TFT-LCD device without the PI film, the LC molecules will be in direct contact with inorganic materials on the panel. Hence, in order to achieve the purpose of controlling orientation of the LC molecules, it is necessary to provide a material for a self-aligning agent with a polymerizing group.

SUMMARY OF THE INVENTION

The purpose of the present disclosure is to provide a material for a vertical aligning agent. A structure of the material comprises a polar anchoring group, a polymerizable group, an intermediate rigid group, and a terminal flexible group. A main role of the anchoring group is to anchor the material on a surface of a non-polar substrate with a polar group thereof by a physical manner. The polymerizable group is mainly a dense polymeric film layer formed by polymerization under an action of ultraviolet (UV) light. The intermediate group and the terminal group mainly act as a three-dimensional barrier to enable liquid crystal molecules to be aligned vertically, which is similar to a role of a PI branch.

According to one aspect, the present disclosure provides a self-aligning material, and a molecular structure of the material is shown in formula (I):

wherein Q is a polar anchor group, L1 is a rigid group, P is a polymerizable group, L2 is a linking group, R is a terminal flexible group, and n is in a range from 1 to 3.

According to one preferred embodiment of the present disclosure, the polar anchor group Q is any one selected from a group consisting of amine, —OH, —COOH, —SH, —CN, —Si(CH$_3$)$_3$, —Si(OCH$_3$)$_3$ and —SiCl$_3$.

According to one preferred embodiment of the present disclosure, the polymerizable group P refers to a polymerizable group under ultraviolet light, which is preferably any one selected from a group consisting of methacrylate, acrylate, vinyl and ethyleneoxy.

According to one preferred embodiment of the present disclosure, the L2 is selected from C$_3$ to C$_{20}$ linear or branched alkylene substituted or unsubstituted by halogen, wherein one carbon atom or more carbon atoms of alkylene can be substituted by one selected from a group consisting of —O—, —CONH—, —COO—, —O—CO—, —CO—, and —CH=CH-group. Preferably, the halogen is F or Cl.

According to one preferred embodiment of the present disclosure, the L1 is

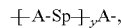

wherein, y is an integer selected from 0 to 5, preferably an integer selected from 0 to 3;

wherein A, which is identical or different from one another, is any one selected from substituted or unsubstituted C$_6$ to C$_{14}$ arylene or C$_4$ to C$_6$ cycloalkylene, and the arylene comprises a group consisting of phenylene, fused-ring arylene, and biphenylene multicyclic aryl. Preferably, a number of C on the cycloalkylene is in a range from 4 to 6. Preferably, A is substituted or unsubstituted biphenylene multicyclic aryl.

Substituents on the A are one or more selected from a group consisting of halogen, cyano, linear C$_1$ to C$_8$ alkyl, and branched C$_3$ to C$_8$ alkyl, wherein one carbon atom or more nonadjacent carbon atoms of the alkyl can be substituted by oxygen or sulfur.

Sp, which is identical or different from one another, is selected from a single bond or C$_1$ to C$_8$ alkyl, wherein one carbon atom or more carbon atoms can be optionally substituted by any one selected from a group consisting of —O—, —S—, —CO—, —CO—O—, —O—CO—, —O—CO—O—, —OCH$_2$—, —CH$_2$O—, —CH=CH—, —CF=CF—, —C≡C—, —CH=CH—COO—, and —OCO—CH=CH—. Preferably, the Sp is a single bond.

According to one preferred embodiment of the present disclosure, the R is selected from C$_2$ to C$_{10}$ alkyl substituted or unsubstituted by halogen, wherein one carbon atom or more nonadjacent carbon atoms of the alkyl can be substituted by oxygen or sulfur. Preferably, the halogen is F.

According to one preferred embodiment of the present disclosure, a molecular formula of the material is

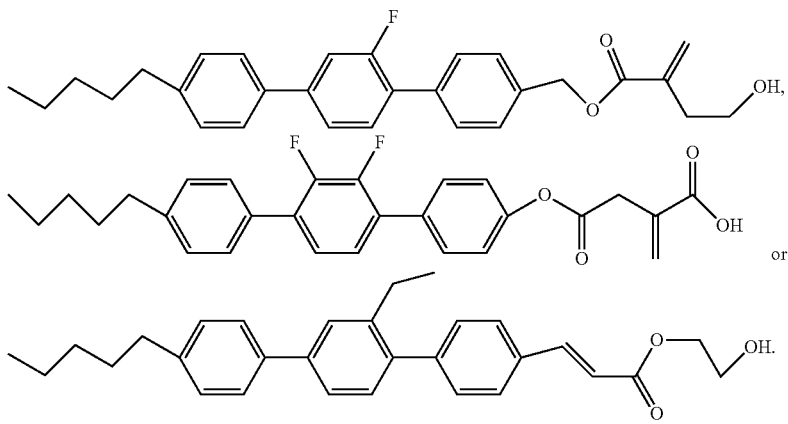

According to the present disclosure, the polar anchor group is connected to the polymerizable group, which is beneficial to increase an aspect ratio of the material. Therefore, a fluid viscosity of the material can be reduced, and a diffusion effect of the material on a substrate can be improved. After irradiation of ultraviolet light, a polymer layer is formed, which improves reliability of the panel.

The material prepared by the present disclosure can replace a PI alignment film in a TFT-LCD device. Therefore, a PI manufacturing procedure can be eliminated and manufacturing cost can be greatly reduced.

BRIEF DESCRIPTION OF THE DRAWINGS

The accompanying drawings provide further understandings of the present disclosure and constitute one part of the description. The drawings are used for interpreting the present disclosure together with the embodiments, not for limiting the present disclosure. In the drawings:

FIG. 1 schematically shows a function of a material in a TFT-LCD device according to the present disclosure.

DETAILED DESCRIPTION OF THE EMBODIMENTS

The present disclosure will be illustrated in detail hereinafter in combination with examples, but the present invention is not limited to the following examples.

Synthesis Example 1

A synthetic route of a first compound is shown as follows.

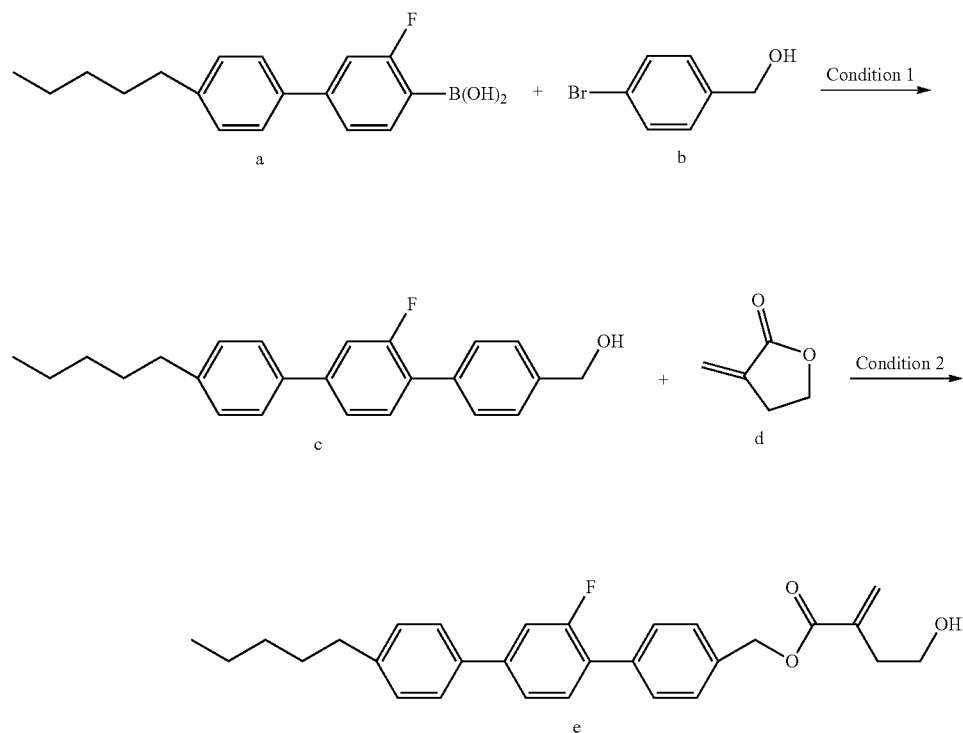

Preparation of an Intermediate Product c:

At room temperature, 20.0 g (67.6 mmol) of a compound a was added to 600 ml of a THF solution, and they were mixed uniformly and cooled to −78° C. Then, 50 mL of n-hexane solution containing 75 mmol of N-butyl lithium was dropwise added thereto and stirred for 10 min. Next, 40 mL of THF solution containing 4 g of ethylene oxide was added thereto (system temperature was 2° C.). Next, 10 mL of trifluoroethyl ester at a temperature of −78° C. was dropwise added and stirred for 15 min. After separation and purification, 11 g of product c was obtained.

Synthesis of a Compound e:

3 mmol of a compound c was added to 3 mmol of a compound d. After uniform mixing, a mixture thereof reacts for 1 h at 110° C. After completion of the reaction, a temperature of a reaction liquid was reduced to 70° C., and then 20 mL of n-hexane was added. The reaction continues for 3 h to obtain a product e after purification.

$H^1$-NMR data of the compound e are as follows: δ: 0.96 (3H), 1.33 (2H), 1.29 (2H), 1.62 (2H), 2.55 (2H), 7.18 (2H), 7.43 (2H), 7.25 (1H), 7.31 (1H), 7.52 (1H), 7.41 (2H), 7.25 (2H), 5.41 (2H), 2.15 (2H), 6.15 (6H), 5.58 (1H), 2.0 (1H).

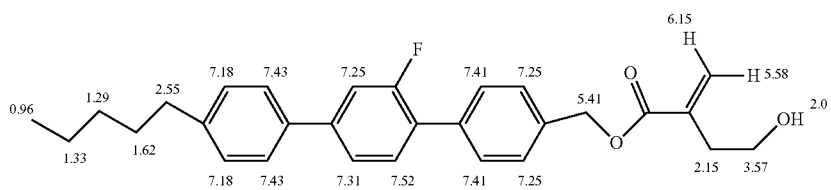

Synthesis Example 2

Synthetic route of a second compound is shown as follows.

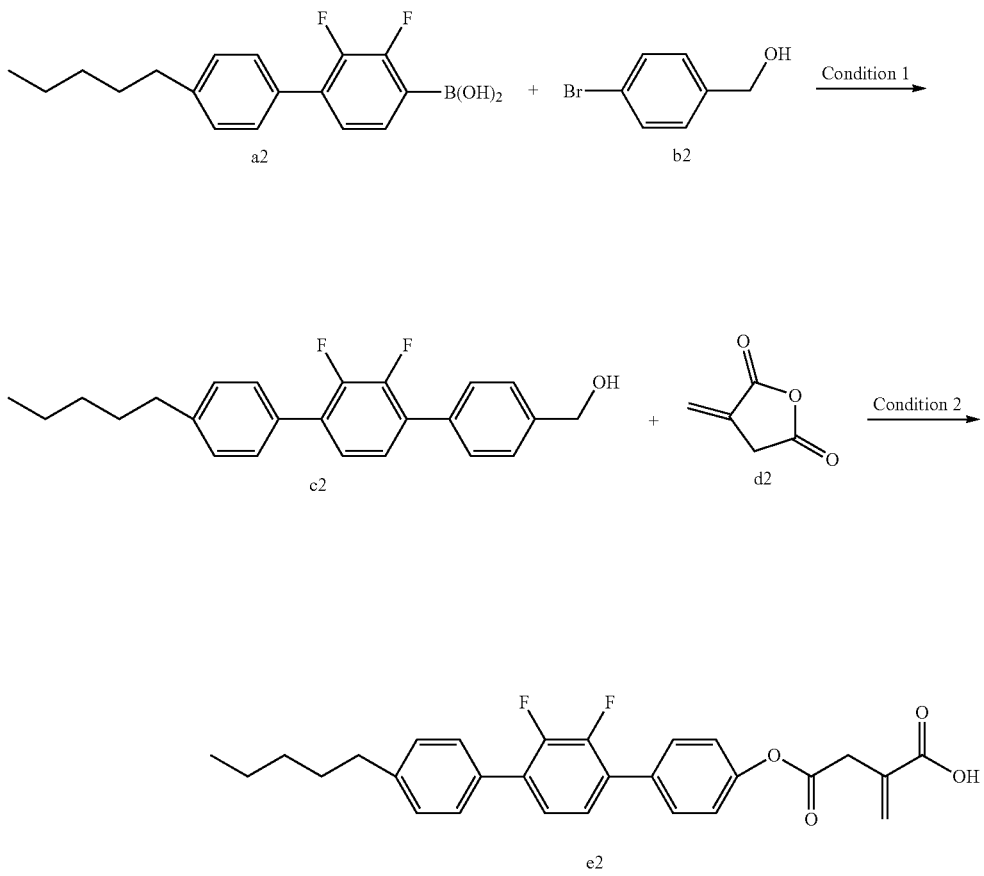

Preparation of an Intermediate Product c2:

At room temperature, 20.0 g (67.6 mmol) of a compound a2 was added to 600 ml of a THF solution, and they were mixed uniformly and cooled to −78° C. Then, 50 mL of n-hexane solution containing 75 mmol of N-butyl lithium was dropwise added thereto and stirred for 10 min. Next, 40 mL of THF solution containing 4 g of ethylene oxide was added thereto (system temperature was 2° C.). Next, 10 mL of trifluoroethyl ester at a temperature of −78° C. was dropwise added and stirred for 15 min. After separation and purification, 11 g of product c2 was obtained.

Synthesis of a Compound e2:

3 mmol of a compound c2 was added to 3 mmol of a compound d2. After uniform mixing, a mixture thereof reacts for 1 h at 110° C. After completion of the reaction, a temperature of a reaction liquid was reduced to 70° C., and then 20 mL of n-hexane was added. The reaction continues for 3 h to obtain a product e2 after purification.

$H^1$-NMR data of the compound e2 are as follows: δ: 0.96 (3H), 1.33 (2H), 1.29 (2H), 1.62 (2H), 2.55 (2H), 7.18 (2H), 7.43 (2H), 7.29 (2H), 7.45 (2H), 7.13 (2H), 5.88 (1H), 6.60 (1H), 2.90 (2H), 11.0 (1H).

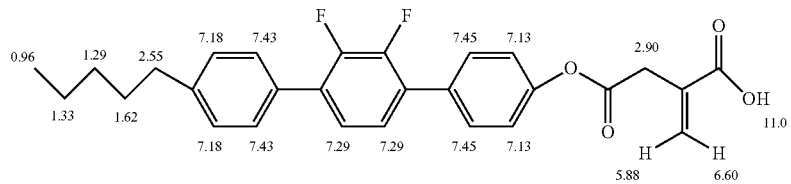 [SMILES: C=C(CC(=O)Oc1ccc(-c2ccc(-c3ccc(CCCCC)cc3)c(F)c2F)cc1)C(=O)O]

Embodiments 1 to 3 and Comparative Embodiment 1

Self-aligning liquid crystal materials used in embodiments 1 to 3 mainly comprise a negative liquid crystal material, a material for a vertical aligning agent, and a polymerizable monomer, and a mass ratio of the three is 97%:2~2.5%:0.5~1%. The negative liquid crystal material is selected from conventional materials in the art. The polymerizable monomer is:

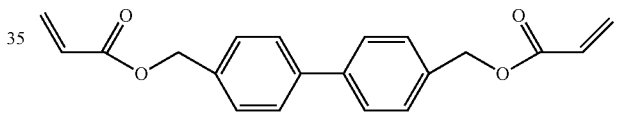

The material for the vertical aligning agent used herein is as shown in Table 1.

TABLE 1

| | Molecular formula of the vertical aligning agent |
|---|---|
| Embodiment 1 | ![structure] |
| Embodiment 2 | ![structure] |
| Embodiment 3 | ![structure] |

A mixed self-aligning liquid crystal material is injected into an empty test panel without PI in vacuum.

In comparative embodiment 1, the prior art is applied. First a PI alignment film is prepared, and then a liquid crystal material is injected.

A comparison results in the embodiments and the comparative embodiment 1 is shown in Table 2.

TABLE 2

|  | Dark state effect | Voltage holding ratio |
| --- | --- | --- |
| Embodiment 1 | good | 99% |
| Embodiment 2 | good | 99% |
| Embodiment 3 | good | 99% |
| Comparative Embodiment 1 | good | 99% |

Conditions for measuring a voltage holding ratio: voltage 1V, frequency 60 Hz, and temperature 60° C.

It can be seen that, when the self-aligning material provided by the present disclosure is applied in an LCD device, an effect equivalent to that of the prior art can be achieved. In the present disclosure, a PI manufacturing procedure can be eliminated and manufacturing cost can be greatly reduced.

The present disclosure is explained in detail in combination with some examples hereinabove, but the examples disclosed herein can be improved without departing from the protection scope of the present disclosure. The technical features disclosed in each and every embodiment of the present disclosure can be combined with one another in any way. In the present description, the situation of the combinations is not described exhaustively in consideration of brevity of length and conservation of resources. Hence, the present disclosure is not limited by the specific embodiments disclosed herein, but includes all technical solutions falling into the protection scope of the claims.

LIST OF REFERENCE NUMBERS

1—Polar anchor group;
2—Polymerizable group;
3—Rigid group;
4—Terminal flexible group; and
5—Liquid crystal molecules.

The invention claimed is:

1. A material for a vertical aligning agent, wherein a molecular formula of the material is

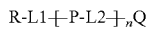

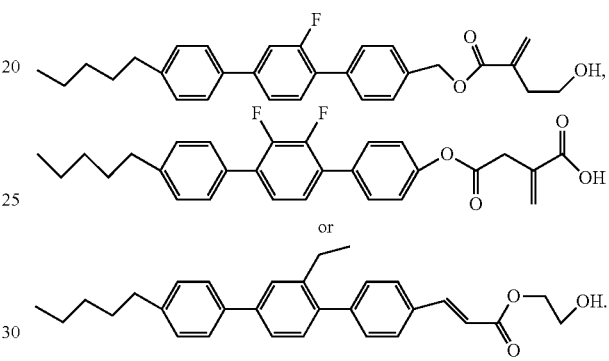

* * * * *